United States Patent
Leonard

(10) Patent No.: US 7,297,534 B2
(45) Date of Patent: Nov. 20, 2007

(54) METHOD OF PLASMID RECOVERY AND APPARATUS FOR DOING SO

(75) Inventor: Jack Thacher Leonard, South Hamilton, MA (US)

(73) Assignee: Millipore Corporation, Billerica, MA (US)

( * ) Notice: Subject to any disclaimer, the term of this patent is extended or adjusted under 35 U.S.C. 154(b) by 289 days.

(21) Appl. No.: 10/404,580

(22) Filed: Apr. 1, 2003

(65) Prior Publication Data

US 2003/0203453 A1 Oct. 30, 2003

Related U.S. Application Data

(62) Division of application No. 09/821,431, filed on Mar. 29, 2001, now Pat. No. 6,759,233.

(60) Provisional application No. 60/197,078, filed on Apr. 13, 2000.

(51) Int. Cl.
*C12N 15/00* (2006.01)

(52) U.S. Cl. ..................... 435/320.1; 436/94

(58) Field of Classification Search ............... 435/270, 435/259, 267

See application file for complete search history.

(56) References Cited

U.S. PATENT DOCUMENTS 5,561,064 A * 10/1996 Marquet et al. ......... 435/320.1
6,277,648 B1 * 8/2001 Colpan ..................... 436/177

FOREIGN PATENT DOCUMENTS

WO          WO9922020     *  6/1999
WO          WO 00/66723   *  9/2000

OTHER PUBLICATIONS

Lyddiatt et al. Biochemical recobery and purification of gene therapy vectors, Current Opinion in Biotechnology 1998 No. 9 pp177-185.*

* cited by examiner

*Primary Examiner*—James Ketter

(57) ABSTRACT

A process for the recovery of plasmids or other DNA from cells using a first filtration step to remove the cellular debris and other large cellular components and then an ultrafiltration step to capture the plasmids or other DNA on the surface of the ultrafiltration membrane where they may be recovered. An apparatus is also taught for enacting the process and comprises an upper microfiltration or coarse filtration membrane and a lower ultrafiltration membrane. The driving force may be the same for both filters or different and may be done sequentially or simultaneously.

12 Claims, 2 Drawing Sheets

US 7,297,534 B2

METHOD OF PLASMID RECOVERY AND APPARATUS FOR DOING SO

CROSS-REFERENCED TO RELATED APPLICATIONS

The present application is a divisional patent application of U.S. patent appliaction No. 09/821,431, filed on Mar. 29, 2001, which claims the benefit of U.S. Provisional Patent Application No. 60/197,078, filed on Apr. 13, 2000. The entire contents of which are incorporated in their entirety herewith.

This application is a division of Ser. No. 09/821,431 filed Mar. 29, 2001 now U.S. Pat. No. 6,759,233 which claims benefit of Ser. No. 60/197,078 filed Apr. 13, 2000.

The present invention relates to a method of plasmid recovery and an apparatus for doing so. More particularly, it relates to a method of plasmid preparation and the devices for accomplishing the method.

BACKGROUND OF THE INVENTION

The conventional method for recovering plasmid from a bacterial lysate after alkaline lysis is commonly known as a bind, wash, and elute process. This process recovers plasmid from a cleared lysate by binding to a glass fiber filter in the presence of a chaotropic agent, such as potassium iodide. This chaotropic agent causes the plasmid to bind to the glass fibers, while most of the other cell constituents pass through. The glass fiber filter is then washed with ethanol (70% or higher by weight) to remove the chaotropic agent. Excess ethanol is removed from the underside of the filter plate by blotting, centrifugation or extensive vacuum drying. The plasmid is then eluted from the glass fibers using water or a low salt buffer.

This method has many drawbacks. First, it introduces a contaminant (ethanol) to the system, which is difficult to fully remove. The residual ethanol may adversely affect the plasmids or the tests performed on them. Additionally, this is a time consuming process and requires many sequential steps. Further, the capacity of the glass fibers to bind the plasmids is limited, making the binding inefficient. Likewise, the elution from the glass is not complete. Some plasmid has been found to irreversibly bind to the glass. In sum, the recovery of the plasmids often is less then 80%, sometimes less then 70% of the available plasmids.

The present invention provides a better method and apparatus for recovering plasmids or other circular DNA which eliminates the introduction of new contaminants, provides for higher plasmid recovery rates with higher purity and which is much faster than the current process.

SUMMARY OF THE INVENTION

The present invention provides a method for rupturing cells, and then filtering the ruptured cells through one or more microfiltration (MF) or coarse filtration membranes. Most cellular debris is removed by the membranes(s) and the remainder is then filtered through an ultrafiltration (UF) membrane so that the plasmids or other DNA is retained on the upper surface of the UF membrane, where it is recovered.

The process may use either centrifugation or a constant pressure differential (positive or negative) to effect both the MF or coarse filtration and UF filtration steps. It is preferred that the process use a constant pressure differential for both steps, and more particularly, it is preferred that a negative constant pressure differential (vacuum) be used in both steps.

Additionally, an apparatus for effecting this process is disclosed. It is comprised of an upper filter plate containing one or more wells, each well(s) having a MF or coarse filtration membrane located within it, preferably adjacent the bottom of the well(s). The upper plate has a connection to a supply for a constant pressure differential. A lower plate is provided which contains one or more wells, each well(s) having an UF membrane located with it, preferably adjacent to the bottom of the wells. The lower plate has a connection to a supply of negative constant pressure differential. Below the lower plate is a liquid waste collector or drain.

It is an object of the present invention to provide a process for recovering plasmids or other DNA comprising the steps of:
(a) disrupting the cell walls sufficiently to free the cellular components, in particular plasmids and other DNA;
(b) filtering the cellular components through one or more microfiltration or coarse filtration membranes or combinations of the two and collecting the filtrate;
(c) filtering the filtrate of (b) through one or more ultrafiltration membranes so as to leave the plasmids or other DNA as a retentate on the upper surface of one or more ultrafiltration membranes; and
(d) recovering the plasmids or other DNA from the upper surface of the ultrafiltration membrane.

It is a further object of the present invention to provide a process for recovering plasmids or other DNA comprising the steps of:
(a) disrupting the cell walls sufficiently to free the cellular components, in particular plasmids or other DNA;
(b) filtering the cellular components through one or more microfiltration or coarse filtration membranes or combinations of the two using a positive pressure to drive the filtration and collecting the filtrate;
(c) filtering the filtrate of (b) through one or more ultrafiltration membranes using a negative pressure to drive the filtration so as to leave the plasmids or other DNA as a retentate on the upper surface of one or more ultrafiltration membranes; and
(d) recovering the plasmids or other DNA from the upper surface of the ultrafiltration membrane.

It is a further object of the present invention to provide a process for recovering plasmids or other DNA comprising the steps of:
(a) disrupting the cell walls sufficiently to free the cellular components, in particular plasmids or other DNA;
(b) filtering the cellular components through one or more microfiltration or coarse filtration membranes or combinations of the two using a positive pressure to drive the filtration and collecting the filtrate;
(c) filtering the filtrate of (b) through one or more ultrafiltration membranes using a positive pressure to drive the filtration so as to leave the plasmids or other DNA as a retentate on the upper surface of one or more ultrafiltration membranes; and
(d) recovering the plasmids or other DNA from the upper surface of the ultrafiltration membrane.

It is a further object of the present invention to provide a process for recovering plasmids or other DNA comprising the steps of:
(a) disrupting the cell walls sufficiently to free the cellular components, in particular plasmids or other DNA;
(b) filtering the cellular components through one or more microfiltration or coarse filtration membranes or combinations of the two using a negative pressure to drive the filtration and collecting the filtrate;

(c) filtering the filtrate of (b) through one or more ultrafiltration membranes using a positive pressure to drive the filtration so as to leave the plasmids or other DNA as a retentate on the upper surface of one or more ultrafiltration membranes; and (d) recovering the plasmids or other DNA from the upper surface of the ultrafiltration membrane.

It is a further object of the presentation to provide a process for recovering plasmids or other DNA comprising the steps of:

(a) disrupting the cell walls sufficiently to free the cellular components, in particular plasmids or other DNA;

(b) filtering the cellular components through one or more microfiltration or coarse filtration membranes or combinations of the two using a negative pressure to drive the filtration and collecting the filtrate;

(c) filtering the filtrate of (b) through one or more ultrafiltration membranes using a negative pressure to drive the filtration so as to leave the plasmids or other DNA as a retentate on the upper surface of one or more ultrafiltration membranes; and (d) recovering the plasmids or other DNA from the upper surface of the ultrafiltration membrane.

It is another object of the present invention to provide an apparatus for recovering plasmids or other DNA comprising an upper filter plate having one or more microfiltration or coarse filtration membranes and a lower filter plate having one or more ultrafiltration membranes, the upper filter plate being located above and adjacent to the lower filter plate.

These and other objects of the present invention will become clear from the description of the invention and the claims.

BRIEF DESCRIPTION OF THE DRAWINGS

FIG. 5 shows a block diagram of a process according to the present invention.

FIG. 6 shows an apparatus for the process of the present invention in cross-section view.

FIG. 7 shows a second apparatus for effecting the process of the present invention in cross-sectional view.

DETAILED DESCRIPTION OF THE INVENTION

Figure 1:
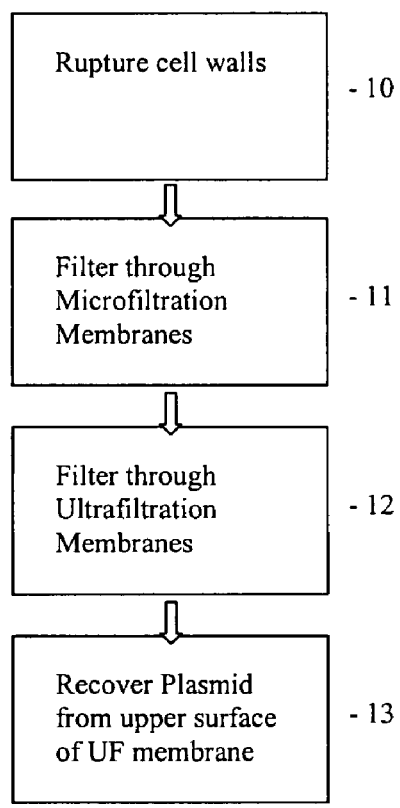
FIG. 1 shows a block diagram of a first preferred process of the present invention.

In FIG. 1 is shown a first embodiment of a process according to the present invention. The first step 10 is to disrupt the cells in question so as to free the plasmid or other DNA material for recovery. This may be done in a variety of ways. The most common method is to use an alkaline lysis procedure in which an alkaline material and detergent containing aqueous fluid such as sodium hydroxide and SDS (sodium dodecyl sulfate) is introduced into the resuspended cell solution causing the cells to lyse.

The lysed cells are then filtered 11 through one or more microporous or coarse filtration membranes to remove the cellular debris such as the cell walls, denatured protein and chromosomal DNA and other large cellular components.

The filtrate is then collected, either on top of an ultrafiltration membrane, if the process is done sequentially, or into a suitable container if the steps are done separately.

The filtrate is then filtered 12 through one or more ultrafiltration membranes so that the plasmids or other DNA are collected on the top of the ultrafiltration membrane. The plasmid or other DNA is then collected for the use, 13.

One or more microfiltration membrane(s) or coarse filtration materials may be used. Typically, one is used, however, a series of two or more membranes may be used to remove all of the cellular debris, especially when the amount of debris is high or the first membrane tends to rapidly clog. If multiple membranes are used, they may be used separately or arranged in sequence to each other, when in sequence, it is preferred that the nominal pore size of each succeeding membrane layer be the same or smaller. In this embodiment, one may use a coarse filter followed by a microporous filter, two coarse filters or two microporous filters.

Typically, nominal pore sizes of these one or more microporous membranes for this application range from about 0.01 microns to about 100 microns, preferably from about 0.05 microns to about 75 microns and more preferably from about 0.1 to about 50 microns.

Typically, the coarse filters have nominal pore sizes of from about 100 microns to about 1000 microns, preferably from about 100 microns to about 500 microns and more preferably from about 100 to about 250 microns.

The microfiltration and/or coarse membrane(s) may be formed from any natural or synthetic polymers, paper, ceramics or metal such as stainless steel or nickel. Preferred polymers useful for making membranes include but are not limited to nitrocellulose, regenerated cellulose cellulose acetate, polysulphones including polysulphone, polyethersulphone, polyphenylsulphones and polyarylsulphones, polyvinylidene fluoride, polyolefins such as ultrahigh molecular weight polyethylene, low density polyethylene and polypropylene, nylon and other polyamides, PTFE, thermoplastic fluorinated polymers such as poly (TFE-co-PFAVE), polycarbonates or particle filled membranes such as EMPORE® membranes available from 3M of Minneapolis, Minn. The membranes may be porous cast membranes, woven or non-woven materials or porous materials formed by other conventional membrane manufacturing methods such as track etching. All of these membranes are well known in the art and are commercially available from a variety of sources including Millipore Corporation of Bedford, Mass.

If desired, these membranes may be treated to render them hydrophilic. Such techniques are well known and include but are not limited to grafting, crosslinking or simply polymerizing hydrophilic materials or coatings to the surfaces of the membranes.

The microfiltration or coarse filtration step may be initiated with any conventional process such as centrifugal force, gravity or a constant pressure differential (such as positive pressure or a vacuum) as is taught by U.S. Ser. No. 60/132,369, filed May 5, 1999 and U.S. Ser. No. 60/182,357, filed Feb. 14, 2000, the teachings of which are incorporated herein in their entireties.

By "constant pressure differential" it is meant either a positive pressure or negative (or vacuum) pressure. Unlike the pressure of the centrifugal method in which the pressure is always decreasing over time due to a reduction in head height of the liquid, in a constant pressure differential process the pressure acting on the liquid can remain constant over the filtration cycle. Additionally, as the pressure is independent of head height of the liquid on which it is acting it may even be increased over time in order to drive the filtration process to completion. It is also within this definition to have a decrease in pressure over time if desired, however unlike in centrifugation, this decrease is controlled and is independent of head height of the liquid thus reducing or eliminating unintentional flux decay.

In this method, a constant pressure differential force is applied to the liquid in the device and the constant pressure differential becomes the driving force for the filtration process rather than the traditional g-force of centrifugation. When using a positive pressure differential (positive pressure), it is typically applied to the topside of the liquid to drive the liquid through the membrane. When a negative pressure differential or vacuum is used, the pressure is typically applied to the downstream side of the membrane so as to act on the bottom of the liquid and draw it through the membrane.

The level of force (whether positive or negative) applied depends upon a number of factors among them are: the amount of sample to be filtered, the type of membrane used (the pore size or molecular cutoff of the membrane, its strength and thickness), the active filtration area of the membrane, the speed at which the filtration is to occur and the level of polarization of the sample.

Unlike centrifugal filtration, constant pressure differential filtration is completely independent of the ability to achieve and maintain a head height meaning that the process is not typically subject to any flux decay at non-polarizing concentrations of solute. Typically, with small volumes, the consequence is that much higher concentration factors are achievable with constant pressure differential driven ultrafiltration relative to what can be achieved with centrifugation within the same amount of time.

Normally, the volumes of liquid in which this process can be used will vary, with a high value of about 2 milliliters. More typically, it is used with volumes of less than 1 milliliter and preferably below 0.5 milliliters (500 microliters). There is an upper limit at which, due to sufficient head height, centrifugation is just as quick as the constant pressure differential process (the exact level is dependent among other things upon the fluid used and the level of constant pressure differential and centrifugation used). However, as will be explained below in conjunction with diafiltration, even when the rates are clearly faster for centrifugation, there are other compelling reasons for still using the process of the present invention rather than centrifugation as it eliminates or lessens the need for diafiltration.

At lower volumes, it is clear however that use of the constant pressure differential is clearly faster than that of centrifugation. The point at which the constant pressure differential process is faster than centrifugation is hereinafter referred to as the "breakthrough point". When using small volumes, about 0.300 milliliters, the present process is about 60% faster than centrifugation.

The effect obtained can be varied by varying the level of the constant pressure differential has on the process. For example, a 3.5 fold increase (3.5×) in the constant pressure differential over that normally applied (1×) results in an almost 6 fold (6×) increase in filtration speed. Additionally, the breakthrough point occurs at about 1 minute with the increased (3.5×) differential as compared to 7 minutes for that of an unchanging (1×) pressure constant differential.

Flux decay may occur in filtering materials that have a high level of polarizing characteristics. In those instances, some flux decay may be observed during filtration by the present process, but this is independent of head height and has to do with the inherent properties of the material being filtered. This means that smaller starting quantities of sample may be used and high levels of ultrafiltration and recovery can be achieved at satisfactory rates even with the presence of such polarizing materials, something that is not always possible with centrifugal processes.

The constant pressure differential may be negative, e.g. a reduced pressure (e.g. below atmospheric or a vacuum) or positive (e.g. above atmospheric).

Typically, a negative constant pressure differential or vacuum force of from about 5 inches Hg to about 27 inches Hg can be used (169–914 millibars). More preferably from about 10 to about 27 inches (338–914 millibars) can be used. The level of vacuum force can be easily varied by the user to fit the desired parameters of the system, the rate of ultrafiltration desired and the sample one is using.

Typically, a positive constant pressure differential of from about 5 to about 80 psi can be used. Higher pressures may be used with devices that have the strength to withstand such pressures. More preferably, from about 40 to about 60 psi can be used. The level of positive pressure can be easily varied by the user to fit the desired parameters of the system, the rate of ultrafiltration desired and the sample he/she is using.

The amount of starting fluid to be filtered can vary widely. However this process has been found particularly useful with small volumes of liquid which cannot typically generate or maintain a suitable head height. Such volumes are generally under about 1000 microliters, preferably less than about 500 microliters and even may be less than 1 microliter.

An additional advantage of the process is that the need for diafiltration (reduction of salts or contaminants by repeated dilutions in ultrapure water or solvent followed by centrifugal filtration to remove the solvated impurities and salts) can be reduced or eliminated, making this process of particular benefit to the biological research area where such diafiltration steps are time consuming and if not complete, can skew the results obtained.

It has been known that a single pass centrifugation process will not remove all salts and other impurities from a biological sample. Therefore, the normal protocol is to dilute the retentate in ultrapure water or a solvent and re-centrifuge the material one or more times in order to draw out a sufficient volume of these impurities.

It has been discovered that in normal centrifugation, as the volume of liquid above the membrane gets below a certain level, typically below 1 microliter volume, evaporation of the liquid is the primary phenomenon responsible for the removal of the liquid, not ultrafiltration. This is due to the low head height that results in little if any pressure being applied to the remaining liquid and thereby little if any filtration occurring. Because of this, any impurity is simply dehydrated onto the surface of the diafiltration filter. When a reconstituting liquid is added to the retentate, these materials simply dissolve into the reconstituting liquid and remain with the retentate. This explains the need for several diafiltration steps.

It has been discovered that in using the constant pressure differential process, filtration remains the dominant means for removing these impurities (as it is independent of head height in order to function), thereby causing the impurities to pass through the membrane and out of the retentate to a much greater level than can be achieved with centrifugation. Essentially all impurities are removed with the current process in a single pass whereas often less than 90% of all impurities are removed with a single pass using the traditional centrifugation process. This allows one to reduce or to eliminate the need for diafiltration steps after filtration and provides a purer product for further use.

As mentioned above, this process is particularly useful when starting with small volumes as the process is quicker than centrifugation. Additionally when the desire is to remove impurities from a biological sample, this process may be used with larger starting samples even though the filtration time may be longer than that for a centrifugation process as it will result in a purer retentate with fewer if no diafiltration steps. The overall time savings (filtration and diafiltration) can justify the apparent increase in filtration time.

The filtrate from the microfiltration step contains the plasmids, other cellular components and cellular fluids as well as lysing material or aqueous fluid used in either the lysing step or microfiltration step.

The filtrate is then subjected to an ultrafiltration process. The process removes substantially all other components of the filtrate, leaving the plasmids on the surface of the ultrafiltration membranes(s) where they are collected for further use. Any process used to conduct ultrafiltration may be used, including centrifugation, positive pressure, or negative pressure, however it is preferred that a constant pressure differential, either positive or negative or combination of both be used.

One or more ultrafiltration membranes may be used, although one is typically all that is needed.

The ultrafiltration membrane(s) should have a nominal molecular weight cut off (materials over the stated molecular weight predominantly stay on the upstream of the membrane while materials smaller then the stated molecular weight pass or into the membrane) of from about 3000 Daltons to about 300 kiloDaltons depending upon the size of the plasmids or other DNA desired to be recovered.

Ultrafiltration (UF) membranes which may be used in this process can be formed from the group including but not limited to polysulphones, including polysulphone, polyethersulphone, polyphenylsulphones and polyarylsulphones, polyvinylidene fluoride, and cellulose and its derivatives, such as nitrocellulose and regenerated cellulose. These membranes typically include a support layer that is generally formed of a highly porous structure. Typical materials for these support layers include various non-woven materials such as spun bounded polyethylene or polypropylene, paper or glass or microporous materials formed of the same or different polymer as the membrane itself. Such membranes are well known in the art, and are commercially available from a variety of sources such as Millipore Corporation of Bedford, Mass.

Preferred UF membranes include regenerated cellulose or polysulphone membranes such as YM™ or Biomax™ membranes available from Millipore Corporation of Bedford, Mass.

Both the microfiltration and ultrafiltration membranes may be used in the form of one membrane or several membranes which can be run simultaneously. For example, a single membrane may be held in a filter holder, such as the Analytical Stainless Steel Filter Holder, Catalog # XX30 012 40 from Millipore or a Microcon® device from Millipore. A device containing several membranes include the use of several Microcon® devices or a multiple well plate such as a MULTISCREEN™ plate available from Millipore in various numbers of wells, typically 96 or 384 wells per plate. Other multiple well membrane device designs may have from 2 to over 1536 wells per plate. The choice between a single device and multiple device and the number of membranes in the multiple device depends upon the application and the amount of plasmid to be recovered. Typically, the amount needed is rather low in total volume and small single filter devices such as a MICROCON® device or 96 or 384 multiple well devices such as MULTISCREEN® plates are preferred.

The one or more microfiltration and one or more ultrafiltration membranes may be symmetrical or asymmetrical in pore shape (morphology) through the depth of the filter. By symmetrical it means that the pore size varies little from one surface of the membrane to the other. By asymmetrical, it means that the pore size does vary from one side to the other in some manner. Asymmetrical membranes come in a variety of forms and configurations, but generally have a pore morphology from one surface to the other selected from the group consisting of symmetric, asymmetric, isotropic portion followed by asymmetric portion, diverging asymmetric portions such that the smallest pore of the membrane is within the depth of the structure and converging asymmetric portions such that the smallest pore is at one surface and the pore size at the convergence of the two asymmetric layers are smaller than the pores in either of the adjacent asymmetric layers. When in the form of a woven or non-woven, they may have a pore size that varies widely and doesn't classically fall with in the symmetrical or asymmetrical definition. They are often classified as depth filters.

Figure 2:
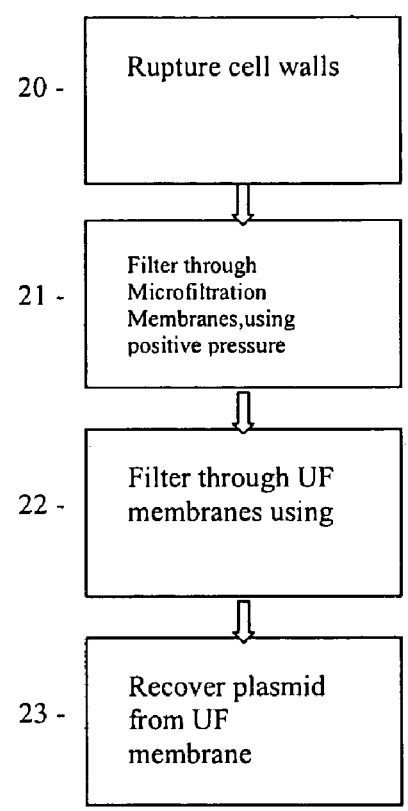
FIG. 2 shows a block diagram of the second preferred process of the present invention.

FIG. 2 shows a second preferred process of the present invention. In this process, the cells are disrupted in step 20 as discussed with the process of FIG. 1, and filtered sequentially through one or more MF and/or coarse filtration membranes of step 21 and are then one or more UF membranes of step 22 by a positive constant pressure differential. The positive pressure may be applied solely to the MF and/or coarse filtration membrane(s) and it will also apply then to the UF membrane if they arranged in a device as shown in FIG. 5 and discussed further below. Alternatively, positive pressure may be applied separately to each step. Plasmids are then recovered from the surface of the UF Filtration step 23.

Typically pressures suitable for effecting the process range from about 0.1 bar to about 6.9 bar, preferably about 0.17 bar to about 0.85 bar. If separate applications of pressure are used in the two filtration steps 21 and 22, then the pressure applied in one step does not need to be the same as that applied in the other step.

Figure 3:
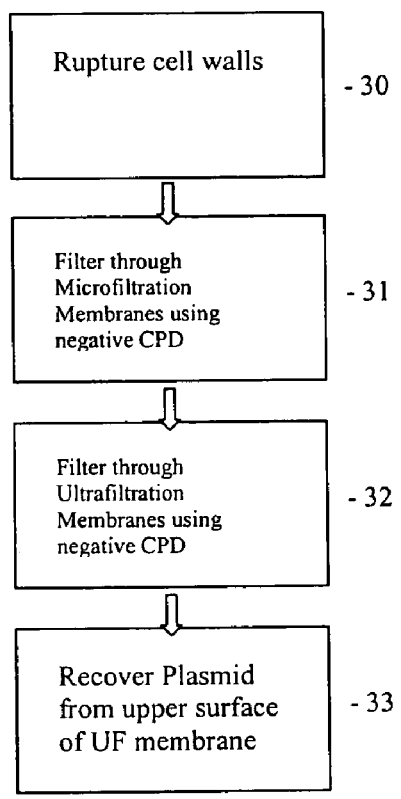
FIG. 3 shows a block diagram of a third process of the present invention.

FIG. 3 shows another embodiment of the present process. In this embodiment, the cell rupturing step 30 is identical to that of the embodiment of FIG. 1. The microfiltration step 31 and ultrafiltration step 32 are both carried out by the use of a negative constant pressure differential (CPD) to the downstream side of each membrane. However, unlike the embodiment of FIG. 2, the negative pressure needs to be applied separately to each of the step 31,32. This is due to the nature of the UF membranes available today which does not allow enough force to penetrate sufficiently through the UF membrane to provide a sufficient force on the MF and/or coarse filtration membrane. However, should such a UF membrane be developed so as to allow for this to happen, then it is the intent of this application to include it within the presently claimed process. Plasmids or other DNA are recovered in step 33.

Figure 4:
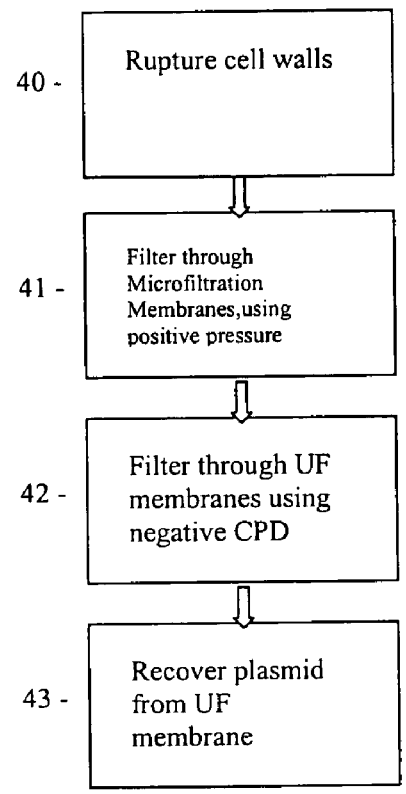
FIG. 4 shows a block diagram of a fourth process of the present invention.

FIG. 4 shows another preferred process of the present invention. In this method, the cell rupturing step 40 occurs as is taught in the embodiment of FIG. 1, the microfiltration step 41 is effected by positive pressure and the ultrafiltration step 42 is effected by negative constant pressure differential. The plasmids or other DNA are then recovered in step 43.

FIG. 5 shows another preferred process in which rupturing the cells 50 occurs as is taught in the embodiment of FIG. 1, the microfiltration step 51 is effected by a negative constant pressure differential and the ultrafiltration step 52 is effected by a positive constant pressure differential. Plasmids or other DNA are recovered in step 53.

Other process forces such as centrifugation may be also be applied in any of the above steps.

FIG. 6 shows an apparatus suitable for carrying out the processing of FIGS. 1–5. In this Figure is a first plate 60 and a second plate 61 arranged so that plate 60 is above plate 61 and removably sealed to it. The upper plate 60 has a cover 62 to which is connected a port 63 for the application of a positive constant pressure differential from a source (not shown) such as compressed air. The port is selectively opened and closed to the source of positive constant pressure differential such as by a valve 64 shown adjacent to port 63, although it is understood that the valve may be located at other positions between the cover and the source of pressure differential or that other known means for varying or stopping the supply to the port may be used.

The upper plate 60 contains one or more membranes, in this example, one membrane 65 selected from coarse membranes and microfiltration membranes or combinations of them is used.

The lower plate 61 contains one or more ultrafiltration membranes 66. A rubber gasket 67 forms the removable seal between the plates although other sealing means known in the art may be used. As shown it is attached to the lower plate 61, although it may be attached to the upper plate 60 or it may be separate from either plate 60 or 61.

A waste receptacle 68 is placed below the lower plate to catch any filtrate through the bottom plate. It may be attached directly to a drain (not shown) or simply be a sump into which the filtrate is passed and then separately disposed of thereafter.

Clamps, screws, or other holder devices may also be used to hold the two plates together during use if desired.

As shown, both plate 60 and 61 show a single well design. It is understood that plates having multiple wells, each well containing a membrane, may be used instead. Plates containing 8, 12, 96, 384, 1536 wells or more are commonly available from sources such as Millipore Corporation and others and are well known.

The device is used as follows. Cells of interest are lysed, either in the upper plate or separately and then transferred into the upper plate. The upper plate having already been attached to the lower plate in a sealed fashion, such as by the use of the rubber gasket and the lower plate is attached to the sump or drain. The cover is attached and the port connected to a supply of positive constant pressure differential such as a supply of compressed air. The pressure is applied to force all liquid and small constituents through the upper plate's membrane and on to the surface of the lower plate's UF membrane. The liquid constituent is then forced through the UF membrane by the same pressure and the plasmids or other DNA are left on the upper surface of the UF membrane. The pressure is cut off and the cover and upper plate are removed and disposed of. The plasmids or other DNA are then recovered from the upper surface of the membrane on the lower plate, such as by rehydrating the plasmids or other DNA and pipetting them off the membrane surface for further processing and analysis.

The above configuration will work when a positive pressure is used, either as a constant pressure differential, centrifugation or otherwise. It will not work with processes that use only negative pressure as the force needed to effect flow through the UF membrane of the lower plate and the upper plate would be so great that the UF membrane would rupture. Likewise it will not work with mixed force methods as it has only one port for the supply of the driving force.

FIG. 7 shows a second apparatus suitable for carrying out the process of FIGS. 1–5 when one uses either negative forces such as vacuum in both filtration steps or a mix of positive pressure in one step and negative pressure in the other step. In this Figure a first plate 80 and a second plate 81 are arranged so that plate 80 is above plate 81 and removably sealed to it although this in not required. The upper plate 80 has a cover 82 to which is connected a first port 83 for the application of a constant pressure differential from a source (not shown) such as compressed air or vacuum. The first port 83 is selectively opened and closed to the source of positive constant pressure differential such as by a valve 84 shown adjacent to port 83, although it is understood that the valve may be located at other positions between the cover and the source of pressure differential or that other known means for varying or stopping the supply to the port 83 may be used.

The upper plate 80 contains one or more membranes, in this example one membrane 85 selected from coarse membranes and microfiltration membranes or combinations of them.

The lower plate 81 contains one or more ultrafiltration membranes 86. A rubber gasket 87 forms the removable seal between the plates although other sealing means known in the art may be used. As shown it is attached to the lower plate 81, although it may be attached to the upper plate 80 or it may be separate from either plate 80 or 81.

A waste receptacle 88 is placed below the lower plate to catch any filtrate through the bottom plate. It may be attached directly to a drain (not shown) or simply be a sump into which the filtrate is passed and then separately disposed of thereafter.

A second port 89 is connected to the lower plate 81 and is used to supply the filtration driving force to the lower plate. The second port 89 is selectively opened and closed to the source of positive constant pressure differential such as by a valve 90 shown adjacent to port 89, although it is understood that the valve may be located at other positions between the cover and the source of pressure differential or that other known means for varying or stopping the supply to the port 89 may be used.

The two ports may be used simultaneously or sequentially (first port then second port) with similar or different forces (e.g. both positive or both negative or one positive and one negative).

Clamps, screws, or other holder devices may also be used to hold the two plates together during use if desired.

As shown, both plate 80 and 81 show a single well design. It is understood that plates having multiple wells, each well containing a membrane, may be used instead. Plates containing 8, 12, 96, 384, 1536 wells or more are commonly available from sources such as Millipore Corporation and others and are well known.

The device is used as follows. Cells of interest are lysed, either in the upper plate or separately and then poured into the upper plate. The upper plate having already been attached to the lower plate in a sealed fashion, such as by the use of the rubber gasket and the lower plate is attached to the sump or drain. The cover is attached and the port connected to a supply of positive or negative constant pressure differential such as a supply of compressed air or a vacuum. The pressure is applied to force all liquid and small constituents through the upper plate's membrane and on to the surface of the lower plate's UF membrane. The liquid constituent is then forced through the UF membrane by the filtration driving force delivered through the second port and maybe the same type of force as is used in the upper plate (such as both being a negative constant pressure differential or both being a positive constant pressure differential) or different (such as one being a negative constant pressure differential and the other being a positive constant pressure differential). The force may be applied first to the upper plate and then to the lower plate (sequentially) or they may be applied at the same time (simultaneously). The plasmids or other DNA are left on the upper surface of the UF membrane. The driving force or pressure is cut off from the lower plate if done sequentially or from both plates if done simultaneously and the cover and upper plate are removed and disposed of. The plasmids or other DNA are then recovered from the upper surface of the membrane on the lower plate, such as by rehydrating the plasmids or other DNA and pipetting them off the membrane surface for further processing and analysis.

EXAMPLE 1

Constant Pressure Differential Method

*E. coli* JM109 carrying pUC19 were inoculated into 1 milliliter aliquots of 2×LB plus appropriate antibiotic in a sterile 96 deep well block (2 ml capacity)(Beckman-Coulter, Fullerton, Calif.). The plates were covered and secured in incubator. They were incubated at 37° C. at 320 r.p.m. for 20 hours.

The deep well block cultures were covered with clear plate tape (Millipore: MATA09600), and centrifuged at 1500×g for 5 minutes. After centrifugation, culture supernatant was immediately decanted to a container for proper disposal. The plates were inverted and tapped firmly on several layers of paper towels on the bench to remove residual culture supernatant.

The pellets were resuspended in 80 µl of Solution 1 (30 mM Glucose; 15 mM Tris-HCl, pH 8; 30 mM Na$_2$EDTA; 60 µg/ml ribonuclease A, all available from Sigma, St. Louis, Mo.) Then, Solution II (0.2 N NaOH; 1% SDS, available from Sigma) was added, and mixed immediately and vigorously with a plate shaker (maximum speed) for 1 min to lyse the cells. The mix was incubated for an additional 2 minutes at room temperature. 80 µl of Solution III (3.6 M Potassium; 6 M Acetate, pH~5, available from Sigma) was added, and mixed immediately and vigorously (maximum speed) with a plate shaker for 2 minutes.

The UF plate was placed in the bottom of the vacuum manifold (Millipore: MAVM 096 OR, or equivalent). The lysate was removed by lowering the pipette tips down the sides of the deep wells through the lysate until reaching bottom. The fluid was pipetted up and down three times. 180 µl of lysate was removed from the bottom of each deep well and dispensed into the corresponding well of a MultiScreen™-NA lysate clearing plate (Millipore: MANANLY50).

Entering the same wells a second time, any residual lysate was removed from the deep well plate, and transferred to the corresponding wells of the lysate clearing plate. The plate was placed on top of the manifold, and the vacuum adjusted to 8 inches of Hg (0.27 bar-203 torr.). The vacuum was applied for 3 minutes, drawing the lysate through the plate and into the UF plate. The first plate was discarded.

The UF plate was removed from inside the manifold and placed on top of the empty manifold and a full vacuum was applied (24 inches of Hg) for 8 min. Filtrate was directed to waste.

200 µl of MilliQ® water was added to each well of the plate. A full vacuum was applied for 4 minutes with the filtrate directed to waste. To dissolve plasmid, 50 µl of TE buffer (10 mM Tris-HCl, pH 8; 1 mM Na$_2$EDTA, available from Sigma) was added to each well of the UF plate. To recover the plasmid, it was resuspended by pipetting up and down 10 times with a liquid handler, and transferred to a v-bottom microplate.

Relative plasmid or other DNA yield was quantified by fluorometric assay. Relative sequencing quality was determined by ET Terminator Sequencing (Amersham Pharmacia Biotech) followed by capillary electrophoresis on MegaBACE® 1000 sequencing system (Amersham Pharmacia Biotech).

EXAMPLE 2

*E. coli* JM109 carrying pUC19 was inoculated into 1 milliliter aliquots of 2×LB plus appropriate antibiotic in sterile 96 deep well blocks (2 ml capacity). The plates were covered and secured in the incubator and incubated at 37° C. at 320 r.p.m. for 20 hours.

The deep well block cultures were covered with clear plate tape (Millipore: MATA09600), and centrifuged at 1500×g for 5 minutes. After centrifugation, the culture supernatant was immediately decanted to a container for proper disposal. The plates were inverted and tapped firmly on several layers of paper towels on the bench to remove residual culture supernatant.

The pellets were resuspended in 80 µl of Solution I first using a plate shaker or vortex, and then by pipette mixing. 80 µl of Solution II was added and mixed immediately and vigorously with a plate shaker (maximum speed) for 1 minute. It was then incubated for an additional 2 minutes at room temperature. 80 µl of Solution III was added and mixed immediately and vigorously (maximum speed) with a plate shaker for 2 minutes.

Separately, 150 µl of Bind Solution was added to each well of a MultiScreen™ plate (Millipore: MAFB N0B 50). The FB plate was placed in the bottom of a vacuum manifold (Millipore: MAVM 096 OR, or equivalent).

To remove the lysate, pipette tips were lowered down the sides of the deep wells through the lysate until reaching bottom and the lysate was pipetted up and down three times. 180 µl of lysate was removed from the bottom of each deep well, and dispensed into the corresponding well of a MultiScreen™-NA lysate clearing plate (Millipore: MANANLY50). Entering the same wells a second time, any residual lysate was removed from the deep well plate, and transferred to the corresponding wells of the MultiScreen™ lysate clearing plate.

The NA plate was placed on top of the manifold, and the vacuum adjusted to 8 inches of Hg (0.27 bar-203 torr.). The vacuum was applied for 3 minutes, drawing the lysate through the NA plate into the FB plate prefilled with Bind Solution. The NA plate was discarded.

The FB plate was removed from inside the manifold and the cleared lysate mixed thoroughly with Bind Solution by rapidly pipetting up and down several times. The FB plate was reattached on top of the empty manifold and full vacuum applied for 1 minute. The filtrate was sent to waste. At this point the plasmid DNA was now bound to the FB plate.

200 µl of 80% ethanol (reagent grade) was added to each well of the FB plate and a full vacuum applied for 1 minute. Filtrate was directed to waste. This step was repeated with vacuum being applied for 3 minutes.

The FB plate was removed from the manifold. The bottom of the plate was cleaned on a clean, lint-free absorbent material. The FB plate was placed on top of a standard microtiter plate with centrifuge alignment frames (Millipore: MACF09604) and centrifuged at 1000×g for 10 minutes to dry. To dissolve plasmid, 70 µl of TE buffer was added to each well of the FB plate, with the TE delivered close to the center of each well. Plasmid was eluted by centrifugation at 1000×g for 5 minutes (eluate volume is typically 45 µl).

|  | Example 1 | Example 2 |
| --- | --- | --- |
| Relative Plasmid Yield | 2X | 1X |
| Relative Sequencing Results | Comparable | Comparable |
| Total Processing Time | 33 min | 50 min |

The present invention provides many advantages over the prior art. First, it reduces the number of steps and time required to recover plasmids or other DNA. Second, it does so without the introduction of contaminants such as ethanol. Additionally, it recovers substantially greater amounts of plasmid or other DNA than the prior system, typically 20 to 30% more on average. Further, if when used with a constant pressure differential driving force in the UF step, the recovered plasmid is purer than that obtained by the conventional process, often containing no salts or other impurities, thus eliminating the need for multiple diafiltration steps. Recovery of the plasmid or other DNA from the top of the ultrafiltration plate, and the elimination of centrifugation make this method more suitable for automation. Lastly, unlike the prior bind/elute process which has capacity limited by the amount of active sites formed on the glass fiber, the present invention has essentially unlimited capacity and may be sealed so as to recover amounts of plasmid or other DNA from femtogram to milligram amounts.

What I claim is:

1. An apparatus for recovering plasmids comprising an upper filter having one or more membranes selected from the group consisting of microfiltration membranes and coarse membranes and a lower filter having one or more ultrafiltration membranes, the upper filter being located above and adjacent to the lower filter and a means for applying one or more driving forces selected from the group consisting of centrifugation and constant pressure differential and combinations thereof to the upper filter and one or more driving forces selected from the group consisting of centrifugation and negative constant pressure differential to the lower filter to effect filtration.

2. The apparatus of claim 1 wherein the filters are sealed liquid tight to each other.

3. An apparatus for recovering plasmids comprising an upper filter plate having one or more wells, each of the one or more wells having one or more membranes selected from the group consisting of microfiltration membranes and coarse membranes and a lower filter plate having one or more wells, each well having one or more ultrafiltration membranes, the upper filter plate being located above and adjacent to the lower filter plate and a means for applying one or more driving forces selected from the group consisting of centrifugation and constant pressure differential and combinations thereof to the upper and the lower filters to effect filtration.

4. An apparatus for recovering plasmids comprising a first filter plate having one or more wells, each of the one or more wells having one or more membranes selected from the group consisting of microfiltration membranes and coarse membranes and a second filter plate having one or more wells, each well having one or more ultrafiltration membranes and a means for applying one or more driving forces selected from the group consisting of centrifugation and a constant pressure differential and combinations thereof to the first filter plate and a means to apply one or more driving forces selected from the group consisting of centrifugation and negative constant pressure differential to the second filter plate to effect filtration.

5. The apparatus of claim 4 wherein the upper and lower filters plates are multiple well plates.

6. The apparatus of claim 1 wherein the driving force applied to the upper filter and the lower filter is centrifugation.

7. The apparatus of claim 1 wherein the driving force applied to the upper filter is a constant pressure differential and the lower filter is a negative constant pressure differential.

8. The apparatus of claim 1 wherein the upper and lower filters each contain more than one filter and are in the form of multiple well plates.

9. The apparatus of claim 1 wherein the upper filter has one or microporous membranes.

10. The apparatus of claim 4 wherein the driving force applied to the first filter plate and the second filter plate is centrifugation.

11. The apparatus of claim 4 wherein the driving force applied to the first filter plate is a constant pressure differential and the second filter plate is a negative constant pressure differential.

12. The apparatus of claim 4 wherein the one or more membranes of the first filter plate is a microporous membrane.

* * * * *